United States Patent
Akca et al.

(10) Patent No.: US 11,646,403 B2
(45) Date of Patent: May 9, 2023

(54) POROUS SHEETS AND METHOD OF MAKING SAME FROM POROUS CARBON NANOTUBES AND DECOMPOSING MICROORGANISMS

(71) Applicants: International Business Machines Corporation, Armonk, NY (US); Aselsan Electronik Sanayi ve Ticaret A.S., Ankara (TR)

(72) Inventors: Esin Akca, Ankara (TR); Cagla Akgun, Ankara (TR); Gokhan Demirci, San Jose, CA (US); Ho-Cheol Kim, San Jose, CA (US); Hareem T. Maune, San Jose, CA (US); Dahyun Oh, San Jose, CA (US); Loza F. Tadesse, Miltona, MN (US); Leslie E. Thompson, San Jose, CA (US)

(73) Assignees: International Business Machines Corporation, Armonk, NY (US); Aselsan Electronik Sanayi ve Ticaret A.S., Ankara (TR)

( * ) Notice: Subject to any disclaimer, the term of this patent is extended or adjusted under 35 U.S.C. 154(b) by 151 days.

(21) Appl. No.: 17/192,892

(22) Filed: Mar. 5, 2021

(65) Prior Publication Data
US 2021/0202928 A1 Jul. 1, 2021

Related U.S. Application Data

(62) Division of application No. 15/243,614, filed on Aug. 22, 2016, now Pat. No. 11,005,089.

(51) Int. Cl.
*H01M 4/13* (2010.01)
*C12N 1/20* (2006.01)
(Continued)

(52) U.S. Cl.
CPC ............. *H01M 4/13* (2013.01); *C01B 32/168* (2017.08); *C12N 1/06* (2013.01); *C12N 1/20* (2013.01);
(Continued)

(58) Field of Classification Search
CPC .......... H01M 4/13; H01M 4/96; H01M 12/08; C01B 32/168; C01B 2202/06; C12N 1/06; C12N 1/20
See application file for complete search history.

(56) References Cited

U.S. PATENT DOCUMENTS

| 5,163,977 | A | * | 11/1992 | Jensvold | ................ | B01D 71/48 96/10 |
| 6,890,436 | B2 | | 5/2005 | Komatsu et al. | | |

(Continued)

FOREIGN PATENT DOCUMENTS

| WO | 03042287 A2 | 5/2003 | | |
| WO | WO-03042287 A2 | * | 5/2003 | ............. A23L 33/25 |

OTHER PUBLICATIONS

Liu et al. "Free-standing, hierarchically porous carbon nanotube film as a binder-free electrode for high-energy Li-O2 batteries", J. Mater. Chem. A, 2013, 1, 12033-12037 (Year: 2013).*

(Continued)

*Primary Examiner* — Steven J Bos
*Assistant Examiner* — Syed T Iqbal
(74) *Attorney, Agent, or Firm* — Karen Canaan; CanaanLaw, P.C.

(57) ABSTRACT

A method of preparing a porous sheet includes mixing a matrix material dispersion including a matrix material dispersed in a first dispersion medium with a microorganism dispersion including microorganisms in a second dispersion medium, to form a mixture. The first and the second dispersion media are removed from the mixture to form a (Continued)

matrix sheet, and the microorganisms are decomposed from the matrix sheet to form the porous sheet.

8 Claims, 13 Drawing Sheets

(51) Int. Cl.
  *C01B 32/168*    (2017.01)
  *C12N 1/06*    (2006.01)
  *H01M 4/96*    (2006.01)
  *H01M 12/08*    (2006.01)

(52) U.S. Cl.
  CPC ........... *H01M 4/96* (2013.01); *C01B 2202/06* (2013.01); *H01M 12/08* (2013.01)

(56) References Cited

U.S. PATENT DOCUMENTS

| | | |
|---|---|---|
| 2004/0241436 A1 | 12/2004 | Hsieh et al. |
| 2005/0191426 A1 | 9/2005 | Moya |
| 2006/0008634 A1* | 1/2006 | Pickrell ................. C03C 11/007 428/305.5 |
| 2009/0309072 A1 | 12/2009 | Hwang et al. |
| 2010/0092371 A1 | 4/2010 | Backov et al. |
| 2015/0232801 A1* | 8/2015 | Yde ......................... A61K 9/19 435/253.4 |

OTHER PUBLICATIONS

Hinds et al. "Aligned Multiwalled Carbon Nanotube Membranes", Jan. 2004, Science, vol. 303 P62-65 (Year: 2004).*

Dorval et al. "Biotemplated Silica and Silicon Materials as Building Blocks for Micro-to Nanostructures" Chem. Mater. 2015, 27, 5361-5370 (Year: 2015).*

Kim et al. "Development of nanosilver and multi-walled carbon nanotubes thin-film nanocomposite membrane for enhanced water treatment", Journal of Membrane Science 394-395 (2012) 37-48 (Year: 2012).*

IBM: List of IBM Patents or Patent Applications Treated as Related, date, pp. 1-2.

Liu et al., Free-standing, hierarchically porous carbon nanotube film as a binder-free electrode for high-energy Li-02 batteries. Journal of Materials Science 1:12033-12037 (2013).

* cited by examiner

POROUS SHEETS AND METHOD OF MAKING SAME FROM POROUS CARBON NANOTUBES AND DECOMPOSING MICROORGANISMS

BACKGROUND

Porous structures benefit diverse systems by facilitating the transport of reactants and increasing the accessibility of reaction sites in extended dimensional scales. In practical applications such as sensors, gas storages, membranes, solar cells and batteries, well established porous structures in a device can directly enhance its performance by improving the liquid or gas flow in a solid frame, thereby maximizing the device efficiency in diverse engineering systems.

For example, free-standing porous carbon sheets have a broad range of applications including battery and solar cell electrodes, gas diffusion layers for fuel cells, separation media and the like. By enhancing the supply of reactants to the reaction sites through interconnected porous structures, reaction efficiency may be improved with conducting carbon frames, which require efficient mass transport in addition to fast kinetics.

Among various approaches to pore generation in solid materials, the direct templating method provides an easy and controllable route to introduce homogeneous pore structures for pore diameters ranging from mesopores (2-50 nm) to macropores (>50 nm). Two general steps are involved in the direct templating method: interaction of pre-existing templates with materials of interest and removal of templates to create pores. Thus, preformed templates should be chemically inert to matrix materials, easy to remove, and cost efficient for mass production.

Since template materials can be expensive and difficult to remove, direct templating methods are often prohibitive for large scale device fabrication. In addition, polymer binders may be generally used to hold the porous structure in a free-standing form, but these polymer binders may increase dead mass in electrodes and cause side reactions during device operations. Further, currently available pore generators, such as silica, polymer beads (e.g., latex), or anodic aluminum oxide, have scale-up limitations for practical applications due to their complicated synthesis process and high material cost.

SUMMARY

In one aspect, the present disclosure is directed to a method of preparing a porous sheet including mixing a matrix material dispersion including a matrix material dispersed in a first dispersion medium with a microorganism dispersion including microorganisms in a second dispersion medium, to form a mixture. The first and the second dispersion media are removed from the mixture to form a matrix sheet, and the microorganisms are decomposed from the matrix sheet to form the porous sheet.

In another aspect, the present disclosure is directed to a method of preparing a porous sheet of carbon nanotubes, including: adding a matrix material dispersion including carbon nanotubes dispersed in a first dispersion medium to a microorganism dispersion including microorganisms dispersed in a second dispersion medium; removing the first and the second dispersion media to generate a sheet of carbon nanotubes, and decomposing the microorganisms from the sheet of carbon nanotubes to form the porous sheet.

In yet another aspect, the present disclosure is directed to a porous sheet including a matrix and a plurality pores in the matrix, wherein the pores consist of cylinders with a diameter of about 0.5 micrometers to about 1 micrometer, and a length of about 1 micrometer to about 5 micrometers.

The details of one or more examples are set forth in the accompanying drawings and the description below. Other features, objects, and advantages of the disclosure will be apparent from the description and drawings, and from the claims.

DETAILED DESCRIPTION

In general, the disclosure describes the use of microorganisms as pore templating materials to generate pores in porous sheets. Microorganisms and matrix materials are dispersed into first and second dispersion media, which may be the same or different. The dispersion medium is removed to form a matrix sheet with spaces or voids occupied by the microorganisms. The microorganisms may be removed from the matrix sheet by thermal or chemical treatments to generate pores inside the matrix at the spaces previously occupied by the microorganisms. The selection and growth of the microorganisms may be controlled to generate matrix sheets with preselected pore sizes, shapes, and concentrations. This technique may be used as a simple, low cost, and binder-free fabrication method for making porous sheets, which may be used in mass production for various applications.

Figure 1:
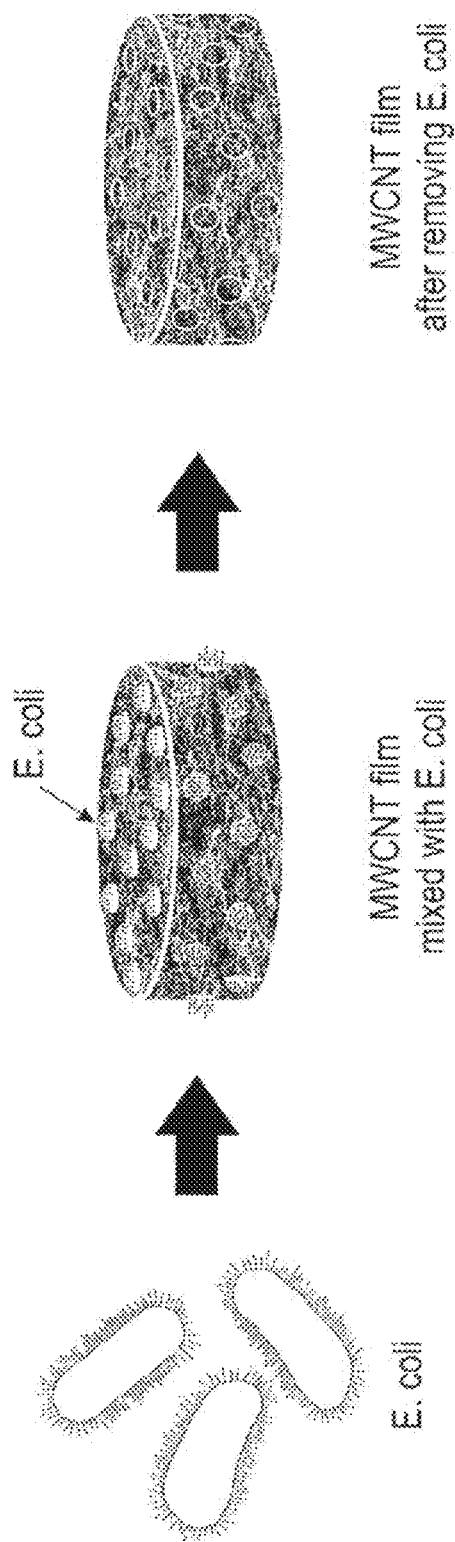
FIG. 1 is an exemplary schematic representation of *E. coli* mediated pore generation for a multiwalled carbon nanotube (MWCNT) film.

FIG. 1 is an exemplary schematic representation of microorganism mediated pore generation for porous sheets using *E. coli* and multiwalled carbon nanotubes. *E. coli* grown or selected for certain pore properties may be present in a multiwalled carbon nanotube film. The *E. coli* act as a pore template for a matrix sheet formed by the multiwalled carbon nanotubes. The *E. coli* may be decomposed to form a porous multiwalled carbon nanotube film. In general, microorganisms may be selected using many of the same selection criteria for which pore templates have been selected in template systems. However, microorganisms may be cheaper to manufacture, easier to remove, more homogeneous, and more environmentally benign. Microorganisms have a relatively low decomposition temperature and are typically cheaper than conventional pore templates.

Figure 2:
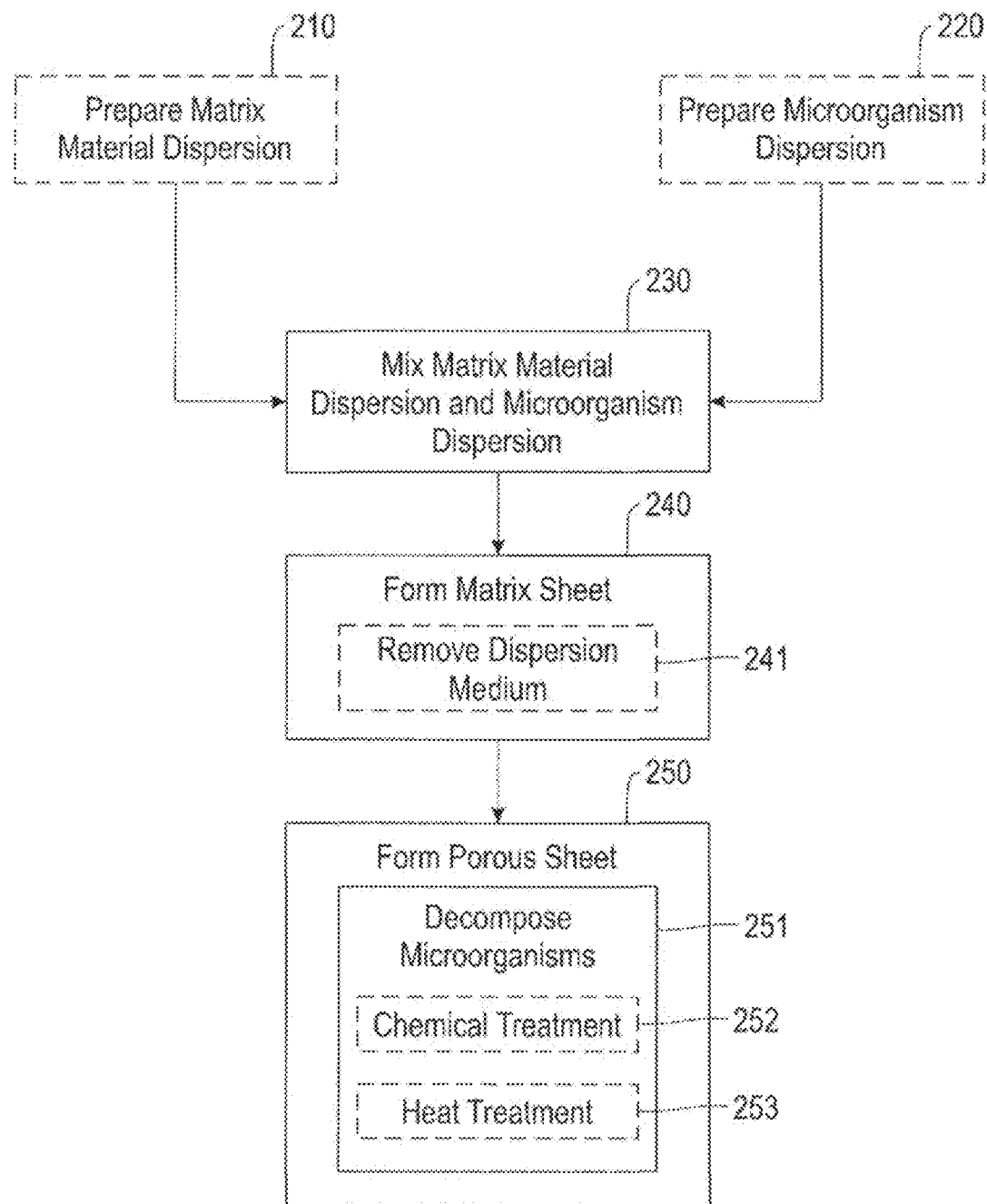
FIG. 2 is a flowchart of a method for producing a porous sheet from microorganisms and matrix materials.

FIG. 2 is a flowchart of a method for producing a porous sheet from microorganisms and matrix materials. A matrix material dispersion may be prepared, as in step 210. The matrix material dispersion may include one or more matrix materials dispersed in a dispersion medium. The matrix materials may be any material capable of dispersing into the dispersion medium and forming a matrix upon dispersion medium removal. The matrix materials may be stably dispersed in medium when they were mixed with microorganism. A variety of matrix materials may be used that include, but are not limited to: nanostructures such as carbon nanotubes and graphene sheets; ceramics; metals; and polymers. In some examples, more than one matrix material may be used. For example, polymers and carbon nanotubes may be used to fabricate a porous composite.

A microorganism dispersion may be prepared. The microorganism dispersion may include microorganisms dispersed into a dispersion medium. The microorganisms may include any microorganism capable of dispersing into the dispersion medium and decomposing in situ from a matrix sheet formed by the matrix materials. In some examples, preparation of the microorganism solution may include dispersing the microorganisms in a growth solution and growing the microorganisms to a desired size and shape. In some embodiments, the microorganisms may be environmentally benign and homogenous in shape. Microorganisms that may be used include, but are not limited to, bacteria such as *E. coli* and *S. epi*, prokaryotic or unicellular eukaryotic organisms including diatoms.

In some examples, the one or more microorganisms may be grown or selected to produce a particular pore size, shape, or combination thereof. Certain microorganism shapes may result in particular pore shapes, such as cylindrical *E. coli* with cylindrical pores and spherical *S. epi* with spherical pores. In some examples, two or more microorganisms having different shapes may be used. Additionally, for pores with a desired volume greater than individual cells, microorganisms may be selected having group configurations. For example, strepto-bacterium may be used to form long chains, which may correlate upon removal to long pores with high surface area in some embodiments, organisms such as fungi may be used. Shapes and configurations that may be selected include, but are not limited to, spherical, rod-shaped, spiral-shaped, curved, paired, grouped, and chains.

In some examples, the one or more microorganisms may be grown or selected to form pores of a particular size. Certain microorganism sizes may correlate with preselected pore sizes, such as *E. coli* for pores with a diameter between 1 and 2 micrometers and a length between 1 and 5 micrometers. As mentioned above, different configurations and groupings of cells may have different sizes, such as clustered *S. epi* for volumes in multiples of their approximately 1 micrometer dimension. In some examples, microorganisms may be in the micron scale and capable of forming macropores having a dimension greater than 50 nm. In some embodiments, the microorganisms have a dimension, such as diameter or length with the scale ranging from 0.1 micrometers to 50 micrometers, or about 5 micrometers to about 25 micrometers, or about 1 micrometer to about 10 micrometers. In some embodiments, which are not intended to be limiting, the pores are cylinders with a diameter of about 0.5 micrometers to about 1 micrometer, and a length of about 1 micrometer to about 5 micrometers.

In some examples, the porosity of the resulting porous sheet may be controlled by the number of the microorganisms in the microorganism dispersion. For example, the added microorganism amounts may correlate with the porosity of the resulting porous matrix sheet.

In some examples, the microorganisms may be grown or selected for a variety of other properties that include, but are not limited to, uniformity, decomposition temperature, chemical resistance, and growth rate. In some examples, the microorganisms can be incorporated with some materials (metals, oxides or other inorganic materials) that can functionalize the matrix materials.

The dispersion medium used in the matrix material dispersion may include any medium capable of dispersing the matrix material. The dispersion medium of the microorganism dispersion may include any medium capable of dispersing the microorganisms. In some examples, the dispersion medium used in the microorganism dispersion may be a growth solution. In other examples, the dispersion medium of the microorganism dispersion may be the same dispersion medium used for the matrix material dispersion medium. In some examples, a dispersion medium may be selected for its removal properties for evaporation or filtration. A variety of dispersion media and combinations thereof may be used including, but not limited to, polar solvents, non-polar solvents, and surfactants.

The matrix material dispersion and the microorganism dispersion may be mixed, as in step 230, to form a mixture having both matrix materials and microorganisms. The mixture may, for example, be mixed to create an evenly dispersed mixture. A matrix sheet may be formed from the mixture, as in step 240. In some embodiments, the matrix sheet may be formed by any mechanism that removes the dispersion medium from the mixture, as in step 241. Mechanisms for removal of the dispersion medium may include filtration and evaporation. The matrix sheet may be further treated to form the matrix sheet. For example, the matrix sheet may be freeze dried, cross-linked, or polymerized to further form the matrix sheet. The resulting matrix sheet may include the matrix materials and the microorganisms distributed to a corresponding porosity. In some examples, the microorganisms are evenly dispersed through the matrix sheet.

A porous sheet may be formed, as in step 250, by removal of the microorganisms from the matrix sheet. In some embodiments, the porous sheet may be formed by decomposing the microorganisms present in the matrix sheet, as in step 251. Decomposition may involve any method that breaks down the microorganisms in the matrix sheet so that the volume of biological material of the microorganisms in the matrix sheet is significantly reduced without collapsing the porous matrix structure. For example, the microorganisms may be decomposed so that they do not provide any significant structural support to the matrix, such as through cellulosic fibers. In some examples, some residual biological material may remain in the matrix without contributing to the structural integrity of the matrix.

The microorganisms can be decomposed by any technique that does not decompose the matrix material including, but not limited to, plasma etching, exposure to ozone, chemical treatments, thermal treatments, and combinations thereof. For example, decomposition of the microorganisms may include chemical treatments, as in step 252, or thermal treatments, as in step 253. Chemical treatments may include any process designed to kill or break down the microorganism in the matrix sheet. For example, chemical treatments may include adding bleach to the matrix sheet at a concentration to kill the microorganisms. Chemicals that may be used include, but are not limited to, ethanol, bases such as sodium hydroxide and bleach, acids such as sulfuric acid, and drying agents. Thermal treatments may include any process designed to kill, burn, combust, or dry biological material from the microorganisms in the matrix sheet. Thermal treatments may include, but are not limited to, baking, burning, thermal calcination, and application of hot air.

The resulting porous sheets may have a matrix with pores, where the matrix material may provide the structure of the matrix sheet and the pores may correspond to the spaces previously filled by microorganisms in the matrix sheet. The porous sheets may be used for a variety of applications, including electronics, filtration, gas separation, and gas storage. The porous sheet may have a variety of configurations, such as thin films, coatings, and membranes.

Figure 3:
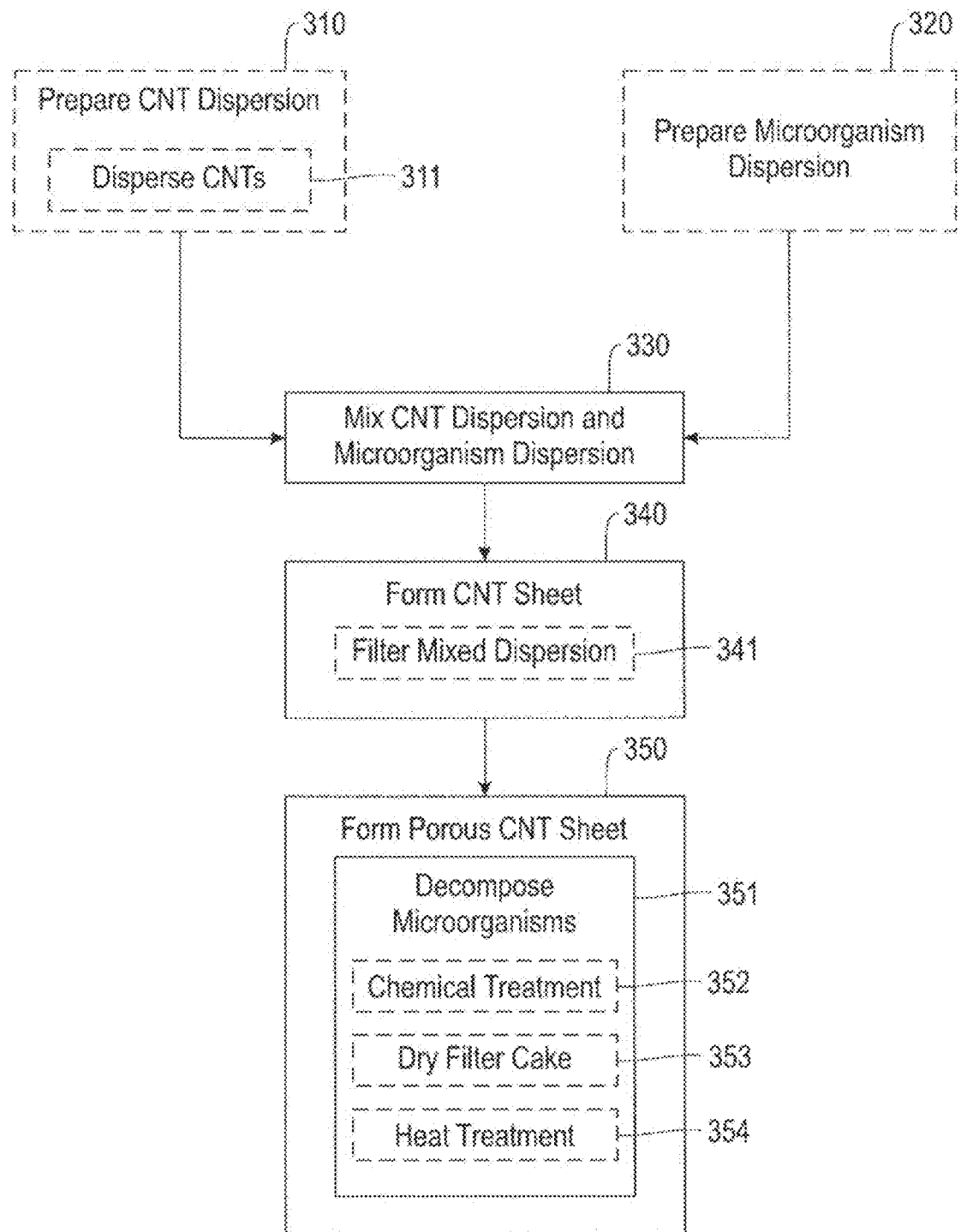
FIG. 3 is a flowchart of a method for producing a porous carbon nanotube (CNT) sheet from microorganisms and CNTs.

FIG. 3 is a flowchart of a method for producing a porous sheet from microorganisms and multiwalled carbon nanotubes (MWCNT). A carbon nanotube dispersion may be prepared, as in 310. Preparation of the carbon nanotube dispersion may include addition of a surfactant and sonication of the carbon nanotube dispersion to reduce agglomeration. A microorganism solution may be prepared, as in step 320. The CNT solution and the microorganism solution may be mixed, as in step 330 to form a mixture. The CNT sheet may be formed from the mixture, as in 340. The mixture may be filtered, as in step 341. The dispersion medium from the mixture may be filtered through a filter, resulting in a dry filter cake having the multiwalled carbon nanotubes and the microorganisms. The porous CNT sheet may be formed, as in step 350, by decomposition of the microorganisms, as in step 251 (351). This decomposition may be done by chemical treatment, as in step 352, and/or thermal treatment, as in step 354. The CNT sheet may be further formed by freeze drying the CNT sheet, as in step 353.

EXAMPLES

Example 1: MWCNT-*E. coli* Film Fabrication

Figure 4:
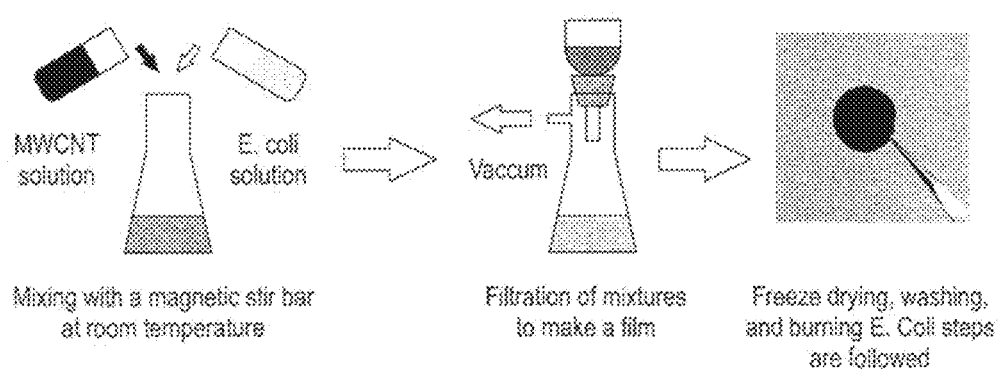
FIG. 4 is an exemplary schematic for a MWCNT-*E. coli* film fabrication process.
Figure 5A:
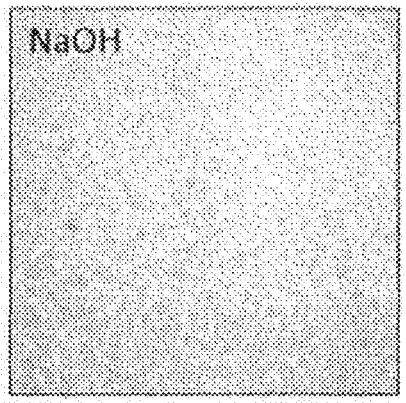
FIG. 5A-5F are exemplary optical microscope images of *E. coli* solutions treated with different chemicals.
Figure 5B:
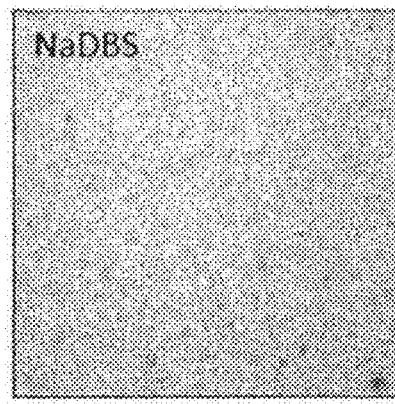
Figure 5C:
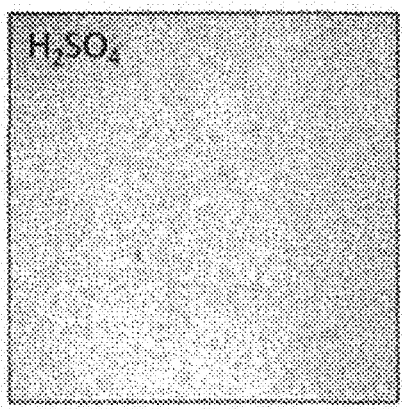
Figure 5D:
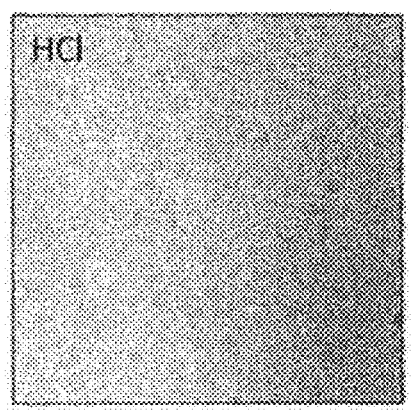
Figure 5E:
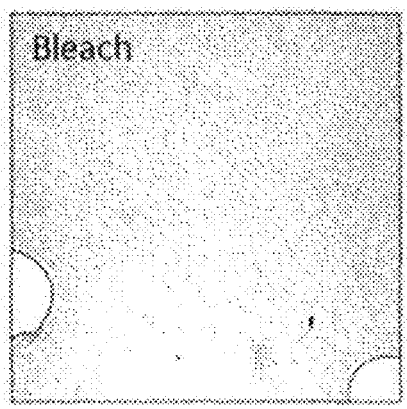
Figure 5F:
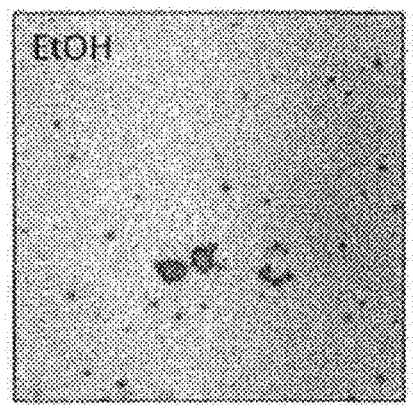

FIG. 4 is an exemplary schematic for a MWCNT-*E. coli* film fabrication process, involving preparation of a MWCNT-*E. coli* mixture, filtration of the mixture, and decomposition of the *E. coli* to form the MWCNT-*E. coli* film.

To prepare the MWCNT-*E. coli* mixture, *E. coli* (Serotype 06, Biotype 1 *E. coli*; available under the tradename ATCC 25922 from ATCC) was grown in tryptic soy broth (TSB) media at 37° C. for 16 hours by ten times dilution of overnight culture to form an E co/i dispersion. The *E. coli* dispersion was dispensed in a dialysis tubing cellulose membrane (available under the tradename D9652-100FT from Sigma Aldrich) and dialyzed overnight in deionized (DI) water to form a dialyzed *E. coli* dispersion. Multiwalled carbon nanotube (MWCNT) powder (12 mg, >95%, OD 15±5 nm, Length 5-20 µm, available from NanoLab Inc.) was dispersed with 0.48 ml (2.5% (w/v)) of sodium dodecylbenzene sulfonate (NaDBS, available from Sigma Aldrich) solution (as the surfactant) and 13.47 ml DI water to form a MWCNT dispersion. The MWCNT dispersion was sonicated by a probe (Model: 102C, available from Branson) in an ice bath for 40 min and the remaining aggregates of MWCNTs were collected by centrifuging at 4000 rpm for 20 minutes. The MWCNT and dialyzed *E. coli* dispersions were then mixed together, at room temperature for 2 hours using a magnetic stirrer at 200 rpm to form a MWCNT-*E. coli* mixture.

To filter the MWCNT-*E. coli* mixture, the MWCNT-*E. coli* mixture was vacuum filtered using an anodisc membrane (Dia. 47 mm, Pore Dia. 0.2 µm, available from Whatman) to form a filtered MWCNT-*E. coli* mixture. The filtered MWCNT-*E. coli* mix, together with the membrane, was first immersed into 10% (v/v) bleach solution for 15 min, and then rinsed overnight in stagnant DI water.

The filtered MWCNT-*E. coli* mix was separated from the membrane in DI water, and then dried via freeze-drying (Labconco Freeze Dry System, Model: Freezone® 4.5, available from Labconco, Inc.) to preserve the 3D interconnected structure and form a MWCNT-*E. coli* film. The obtained MWCNT-*E. coli* film was heat treated in a custom-made quartz tube furnace at 400° C. for 3 hours under 300 sccm $N_2$ flow in order to remove any residual *E. coli*.

Example 2: *E. coli* Chemical Treatment

In some examples, chemicals may be used to decompose microorganisms for removal in forming a porous sheet. FIGS. 5A-5F are optical microscope images of *E. coli* solutions treated with different chemicals. The decomposition of an *E. coli* (~$8.44 \times 10^{10}$ cells in 200 µl) solution was investigated by incubating them in diverse chemicals, such as base (NaOH, 1 M, 600 µl; see FIG. 5A), surfactant (NaDBS, 2.5 w/v %, 600 µl; see FIG. 5B), acid ($H_2SO_4$ (20 v/v %) or HCl (15 v/v %), 600 µl; see FIG. 5C and FIG. 5D, respectively), bleach (10 v/v %, 600 µl; see FIG. 5E) or ethanol (200 Proof, 600 µl, see FIG. 5F) for 2 hours and examining them under an optical microscope.

As seen in the optical microscope images in FIG. 5A-5F, the *E. coli* was most effectively decomposed by bleach solutions (FIG. 5E) compared to other solvents used in these examples.

Figure 6A:
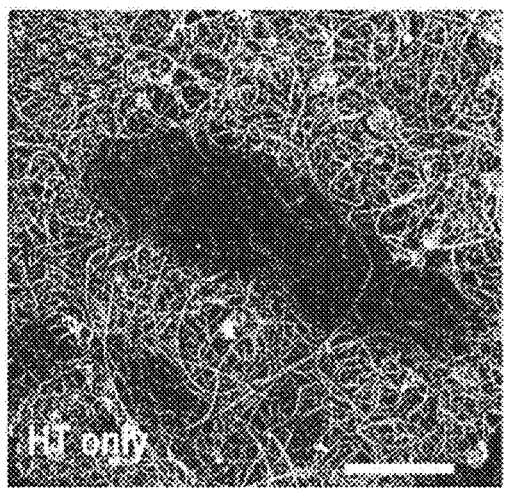
FIGS. 6A-6) are exemplary scanning electron microscope images of MWCNT-*E. coli* films with various chemical and heat treatments.

FIGS. 6A-6D are SEM images of MWCNT-*E. coli* films following various chemical and heat treatments. After pre-screening several solvents to apply in the *E. coli* removal step, MWCNT-*E. coli* films were submerged in 400 ml of each bleach (10 v/v %, 1 h), NaOH (1 M, 1 h), and ethanol (200 Proof, 2 h)/$H_2SO_4$ (20 v/v %, 1 h) solvents and then heat-treated at 400° C. for 3 h under $N_2$. The decomposition of *E. coli* with chemicals and heat-treatment was evaluated with scanning electron microscope (SEM). With the thermal treatment only, most of the *E. coli* residues remained in MWCNT-*E. coli* films as can be seen in FIG. 6A.

Figure 6B:
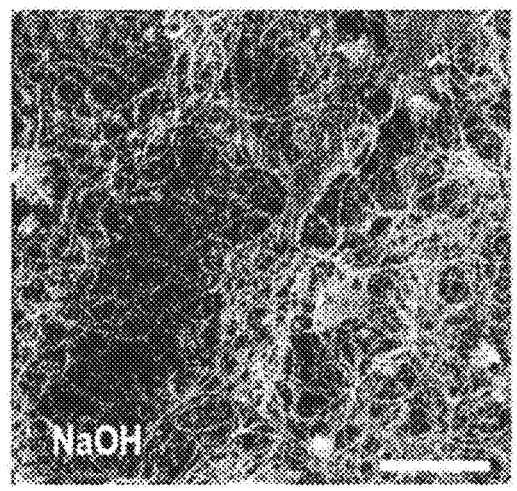
FIGS. 6E-6F are exemplary graphs of XPS and Raman analyses of the MWCNT and MWCNT-*E. coli* films obtained following the treatments of FIGS. 6A-6D.
Figure 6C:
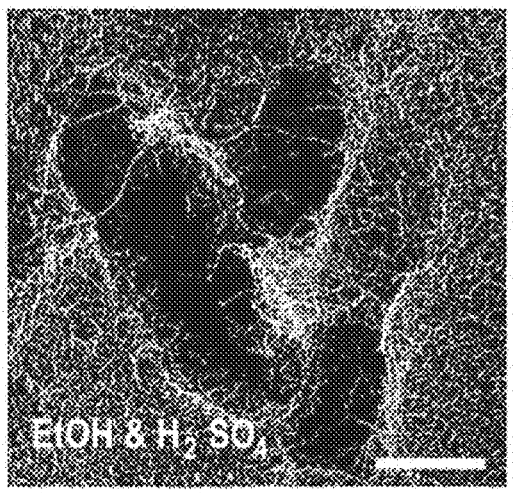
Figure 6D:
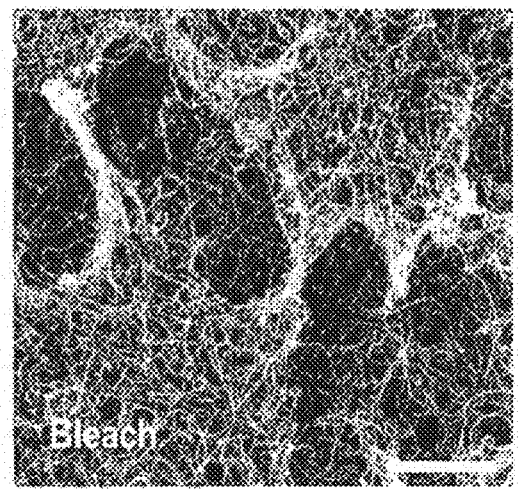

Among the selected removal solvents, MWCNT-*E. coli* films incubated with bleach solutions showed better removals of K coil in films after heat treatment (FIG. 6D), while NaOH and ethanol/$H_2SO_4$ solvents were less effective in decomposing *E. coli* (FIGS. 6B and 6C, respectively). Since the bleach solution contains the strong oxidizer, sodium hypochlorite (NaClO) that can potentially oxidize MWCNT, the incubation time of MWCNT-*E. coli* films were adjusted (15 min of incubation) to lyse the cells, but limited to the extent where the oxidation of MWCNT can be minimized.

Figure 6E:
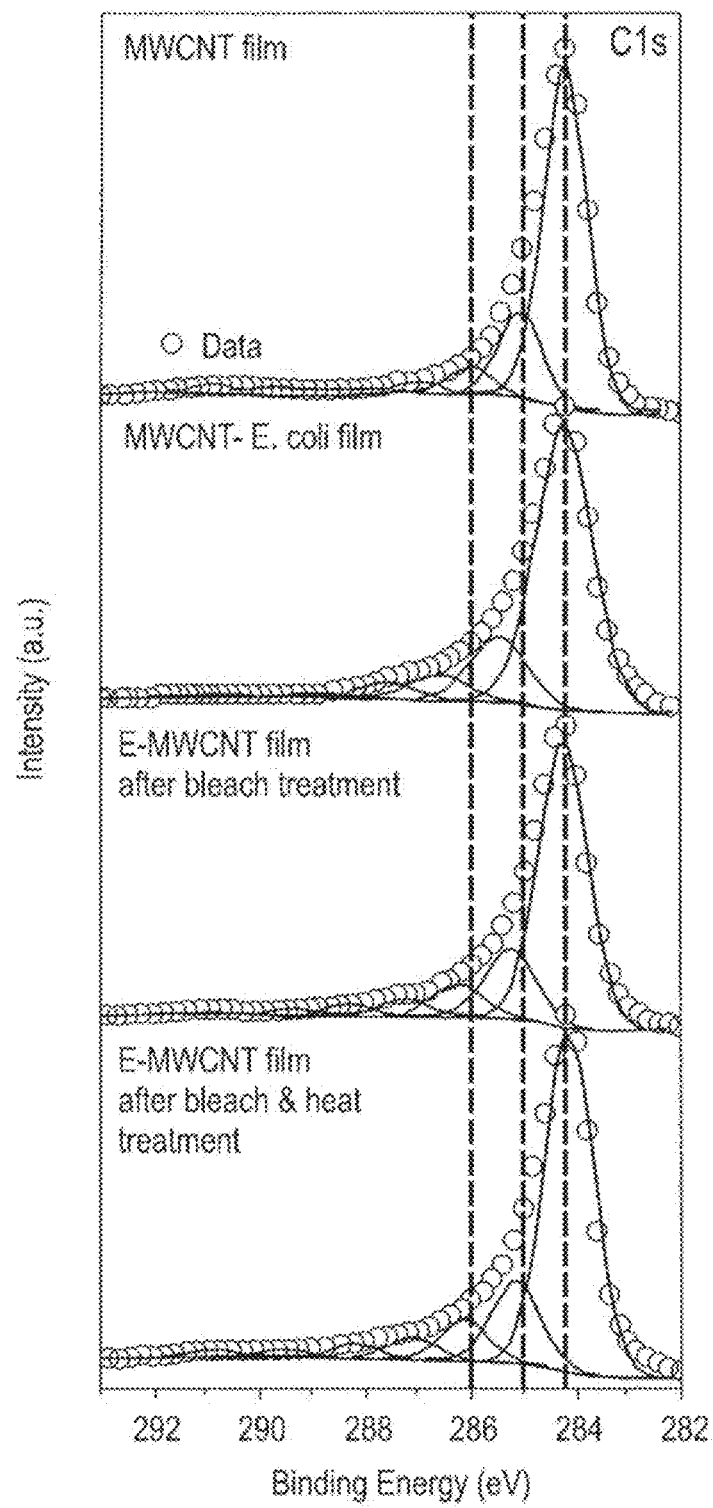

The surface state of MWCNT-*E. coli* films during their fabrication process was investigated with X-ray photoelectron spectroscopy (XPS) and Raman spectroscopy. FIG. 6E is a graph of XPS analyses of MWCNT and MWCNT-*E. coli* films for the treatments in FIGS. 6A-6D. Each spectrum was analyzed by peak deconvolution with a fixed FWHM (full width at half maximum) using CASA XPS software. Carbon bonding was categorized into two groups, the carbon bonding between (1) carbon-carbon ($sp^2$ C═C at ~284.4 eV, $sp^3$ C—C at ~285.5 eV) and (2) carbon-oxygen (C—OH, C=O, COOH, higher than 286 eV) to determine the oxidation of MWCNT. Although a major peak increase higher than 286 eV was not evident in FIG. 6E, the carbon oxidation to generate functional groups increased approximately by 8% from the peak analysis (Table 1).

Figure 6F:
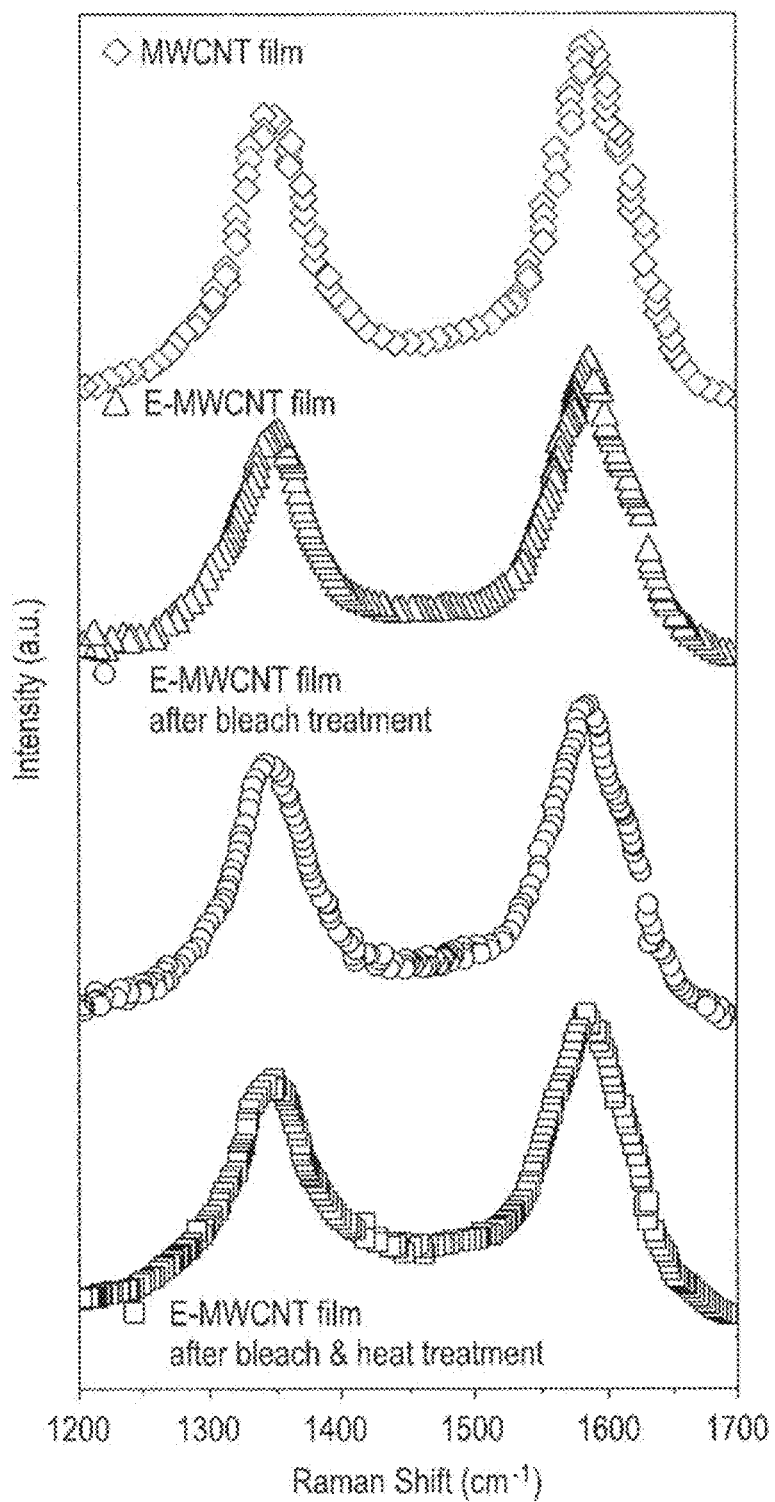

FIG. 6F is a graph of Raman analyses of MWCNT and MWCNT-*E. coli* films for the treatments in FIGS. 6A-6D. The partial (8%) disruption of MWCNT during the porous film fabrication process using *E. coli* was further supported by the similar peak intensity ratio between $I_G$ and $I_D$ in Raman spectra. The D band is known to be attributed to the amorphous carbon of CNT while G band intensity originates from in-plane tangential carbon-carbon stretching bonds. The $I_G/I_D$ ratio varies from 1.203 to 1.255 but the changes are minor during the porous film fabrication process, matching the 8% of carbon bonds changes from XPS results.

Table 1 below is a table of the XPS and Raman analyses of FIGS. 6E and 6F.

TABLE 1

| Sample | XPS C=C & C—C Concentration (%) | Raman G-band (cm$^{-1}$) | Raman D-band (cm$^{-1}$) | $I_G/I_D$ ratio |
|---|---|---|---|---|
| MWCNT film | 88.07 | 1586.88 | 1342.37 | 1.239 |
| E-MWCNT film | 84.52 | 1586.46 | 1350.27 | 1.255 |
| E-MWCNT film (bleach treated) | 83.51 | 1586.90 | 1346.79 | 1.203 |
| E-MWCNT film (bleach + hest treated) | 80.4 | 1581.32 | 1347.44 | 1.253 |

Example 3: Porosity and Pore Shape Control

Figure 7A:
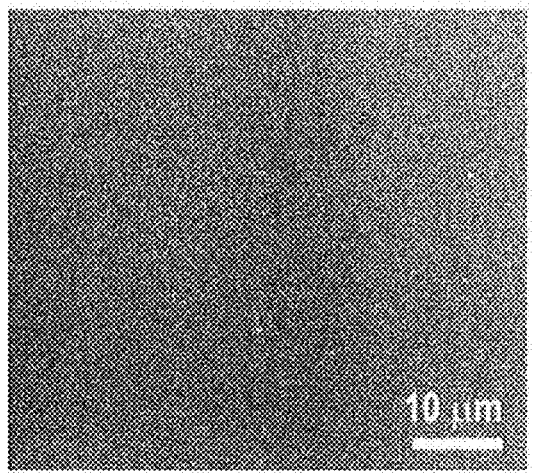
FIGS. 7A-7) are exemplary SEM images of MWCNT films with different pore shapes and porosities.
Figure 7B:
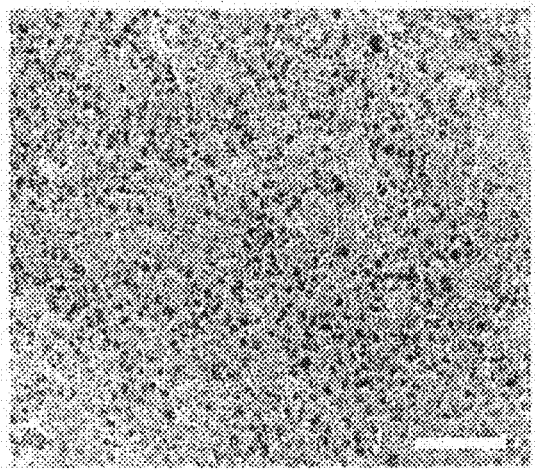
Figure 7C:
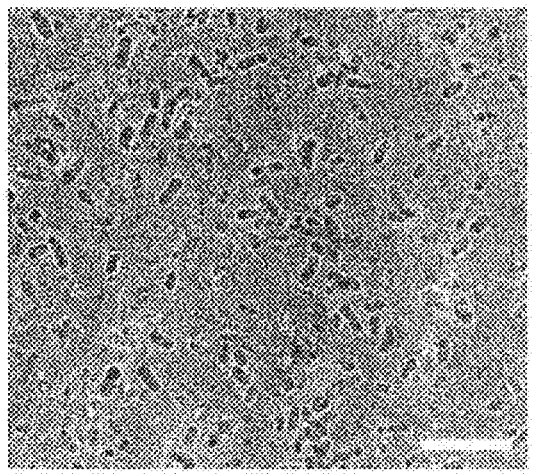
Figure 7D:
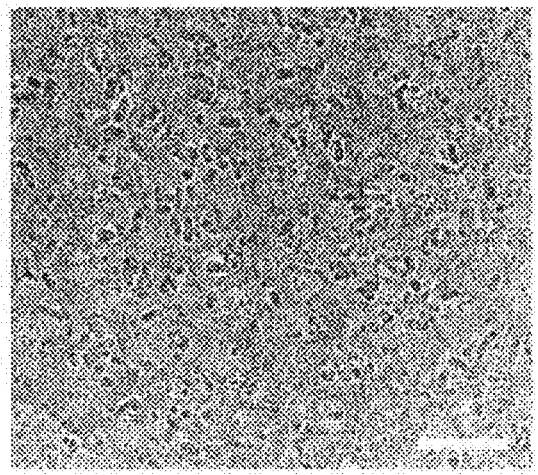

In some examples, porosity and pore shape in porous matrix structures may be controlled through selection and concentration of microorganisms. FIGS. 7A-7D are exemplary SEM images of MWCNT films with different pore shapes and porosities. FIG. 7A is a SEM image of a compact MWCNT film. FIG. 7B is a SEM image of an MWCNT-*S. epi* film having spherical pores. FIG. 7C is a SEM image of an MWCNT-*E. coli* film having cylindrical pores at a first concentration. FIG. 7D is a SEM image of MWCNT-*E. coli* film having cylindrical pores at a second concentration. In contrast to the compact MWCNT film of FIG. 7A, microscale pores were generated with each cylindrical and spherical shapes as can be seen from FIGS. 7C/7D and 7B, respectively, by using cylindrical (named *E. coli* in this work, Serotype O6, Biotype 1 *E. Coli*; available under the tradename ATCC 25922 from ATCC) and spherical (named *S. epi* in this work, *Staphylococcus epidermis*; available under the tradename ATCC 358914 from ATCC) shape bacteria as pore templates. In addition, pore volumes (porosity) can be controlled by adjusting the input amount of microorganism used during the fabrication process. The cell amount added was controlled by measuring the optical density (OD) of culture solution at 600 nm with UV spectroscopy. The pore populations in MWCNT film were varied by controlling the *E. coli* amount, such as ~2.76×10$^{10}$ cells for FIG. 7C, and ~8.19×10$^{10}$ cells for FIG. 7D.

Figure 8A:
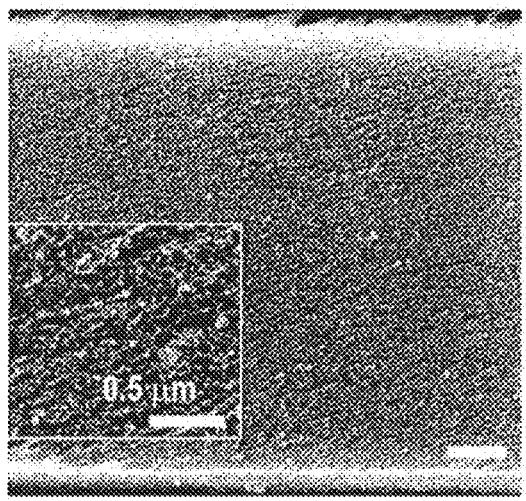
FIGS. 8A-8F are exemplary SEM images of a MWCNT film and a MWCNT-*E. coli* films after battery discharge.
Figure 8B:
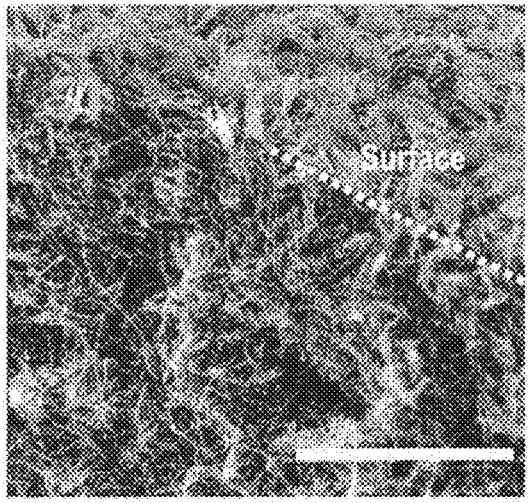
Figure 8C:
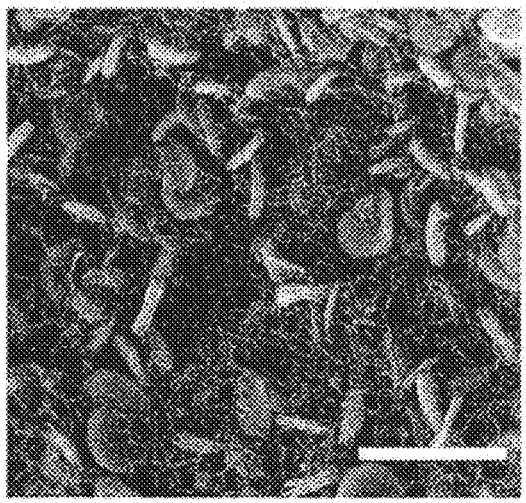
Figure 8D:
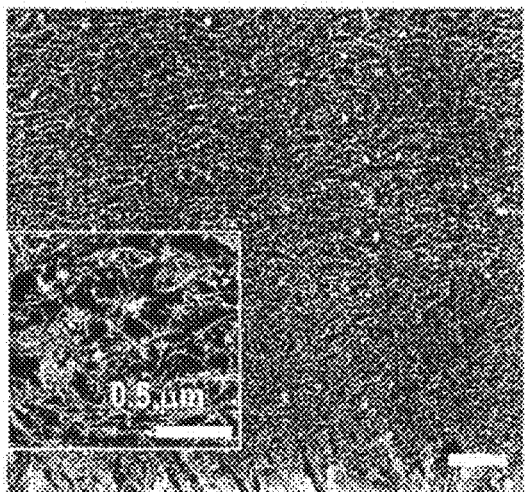
Figure 8E:
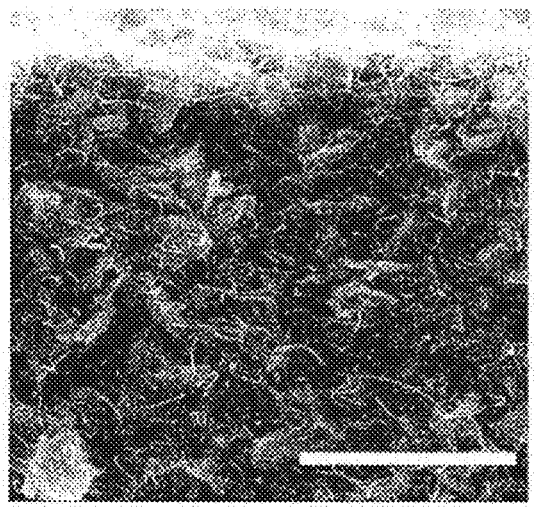
Figure 8F:
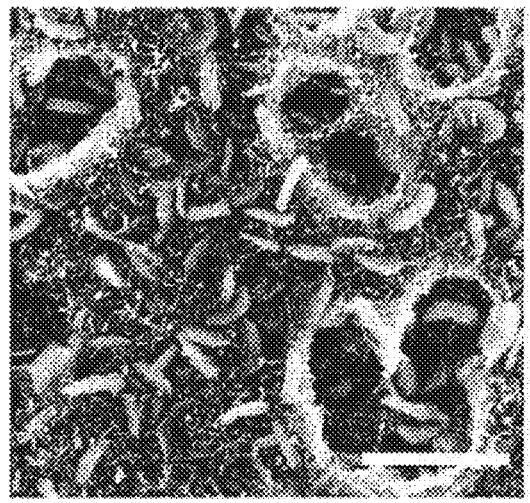

Example 4: Application of Porous MWCNT-*E. coli* Films for Li—O$_2$ Battery Cathodes In some examples, porous films with pores formed by microorganisms may be used for electronics applications. FIGS. 8A-8F are exemplary SEM images of a MWCNT film and a MWCNT-*E. coli* film after battery discharge. MWCNT films (FIGS. 8A-8C) and MWCNT-*E. coli* films (FIGS. 8D-8F) were applied as free-standing binder-free cathodes to utilize their porous 3D structures for Li-oxygen batteries. Since the interconnected porous structure may promote the supply of reactants throughout the cathode thickness, homogeneous distribution of discharge products (Li$_2$O$_2$) was observed after Li-oxygen battery discharge. To make an observation of Li$_2$O$_2$ after discharge, toroidal growth of Li$_2$O$_2$ was investigated by using electrolytes with 4000 ppm of HO in 1 M LiTFSI (lithium bis(trifluoromethane sulfonyl) amide)/DME (1,2-Dimethoxyethane) (available from BASF Corp.). While the toroidal Li$_2$Oz was only observed on the surface of MWCNT electrode film as seen in FIGS. 8I and 8C, E-MWCNT electrodes showed homogeneous distributions of toroidal Li$_2$O$_2$ throughout their thickness after discharge as seen in FIGS. 8E and 8F.

Figure 9A:
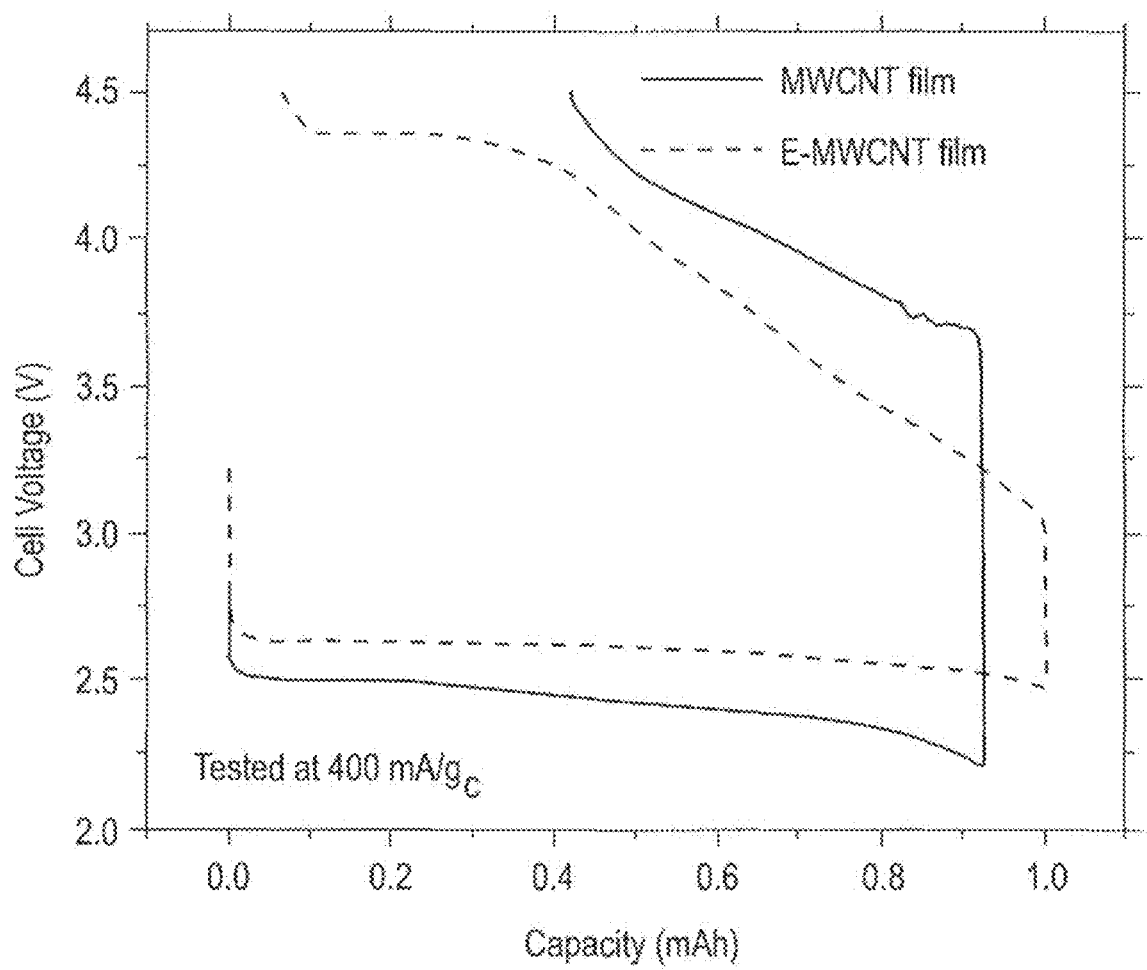
FIG. 9A is the first Li-oxygen battery galvanostatic cycle profile graph of MWCNT and MWCNT-*E. coli* films.
Figure 9B:
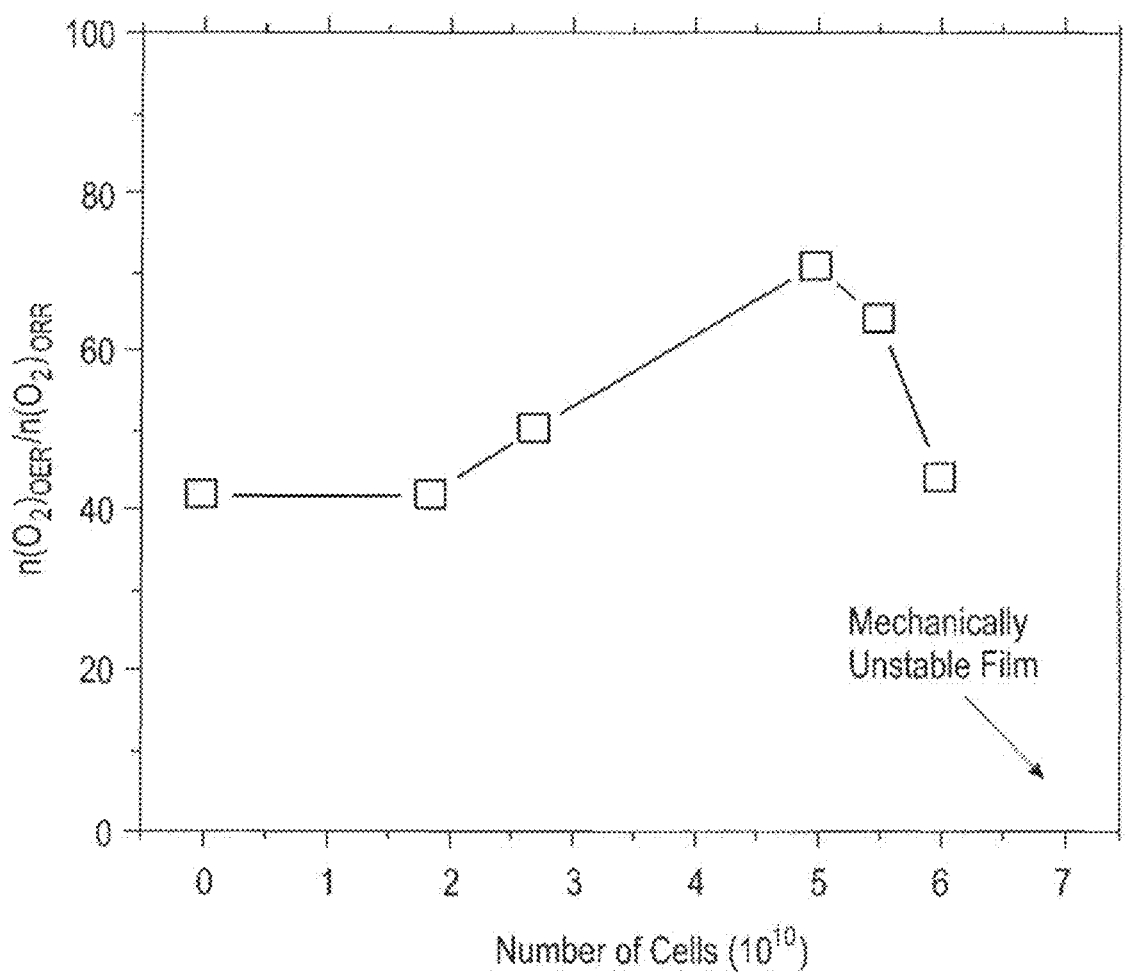
FIG. 9B is a graph of oxygen recovery ratio of MWCNT-based electrodes with different porosities.

FIG. 9A is a galvanic cycle profile graph of the MWCNT and MWCNT-*E. coli* films of FIGS. 8A-8F. The better utilization of electrodes also contributed to decrease the overpotential during battery cycling as can be seen from FIG. 9A. In a given operation potential window maintaining electrolyte stability (2.2-4.5 V vs. Li/Li$^{+1}$), E-MWCNT electrodes achieved 93.5% of coulombic efficiency while MWCNT electrodes showed only 54.25%. This poor recharging ability of MWCNT electrodes also presented lowered oxygen recovery ratio, 41.83% (ratio between the number of oxygen gas moles created during charging and oxygen gas used during discharge, $(O_2)_{OER}/n(O_2)_{ORR}$, %) measured by differential electrochemical mass spectrometry (DEMS). FIG. 9B is a graph of oxygen recovery ratio of the MWCNT-*E. coli*-based electrodes with different porosities. By adjusting the porosity to achieve maximum oxygen recovery ratio, E-MWCNT electrodes showed 70.56% of recovery efficiency in a Li-oxygen battery, as seen in FIG. 9B.

Various examples have been described. These and other examples are within the scope of the following claims.

What is claimed is:

1. A method of preparing a porous sheet of carbon nanotubes, comprising:
    adding a matrix material dispersion comprising carbon nanotubes dispersed in a first dispersion medium to a microorganism dispersion comprising microorganisms dispersed in a second dispersion medium;
    removing the first and the second dispersion media to generate a sheet of carbon nanotubes; and
    decomposing the microorganisms from the sheet of carbon nanotubes to form the porous sheet, wherein the decomposing comprises chemical treatment followed by freeze drying followed by thermal treatment.

2. The method of claim 1, wherein the porous sheet includes multi-walled carbon nanotubes.

3. The method of claim 1, wherein the microorganisms include *E. coli*.

4. The method of claim 1, wherein the decomposing includes a bleach treatment followed by thermal calcination.

5. The method of claim 1, wherein the microorganisms have a dimension of about 0.1 micrometers to about 30 micrometers.

6. The method of claim 1, wherein the microorganisms have a dimension of about 0.1 micrometers to about 5 micrometers.

7. The method of claim 1, wherein the matrix sheet includes spaces filled by the microorganisms, and wherein said decomposing the microorganisms forms pores in the porous sheet that correspond to the spaces.

8. The method of claim 1, wherein the first dispersion medium and the second dispersion medium are different.

* * * * *